United States Patent
Wang et al.

(10) Patent No.: US 9,823,216 B2
(45) Date of Patent: Nov. 21, 2017

(54) SENSOR MATERIAL AND GAS SENSOR ELEMENT AND GAS SENSOR DERIVED THEREFROM

(71) Applicant: DELPHI TECHNOLOGIES, INC., Troy, MI (US)

(72) Inventors: Da Yu Wang, Troy, MI (US); David M. Racine, Davison, MI (US); Sheng Yao, Troy, MI (US)

(73) Assignee: DELPHI TECHNOLOGIES, INC., Troy, MI (US)

( * ) Notice: Subject to any disclaimer, the term of this patent is extended or adjusted under 35 U.S.C. 154(b) by 195 days.

(21) Appl. No.: 14/565,896

(22) Filed: Dec. 10, 2014

(65) Prior Publication Data
US 2016/0169831 A1   Jun. 16, 2016

(51) Int. Cl.
*G01N 27/407*   (2006.01)

(52) U.S. Cl.
CPC ..... *G01N 27/4075* (2013.01); *G01N 27/4076* (2013.01)

(58) Field of Classification Search
CPC ... G01N 27/403–27/41; G01N 27/417–27/419
USPC ............... 204/421–429; 73/23.31–23.32; 205/780.5–781, 783.5–785
See application file for complete search history.

(56) References Cited

U.S. PATENT DOCUMENTS

| | | | | |
|---|---|---|---|---|
| 5,897,759 A | * | 4/1999 | Kurosawa | G01N 27/4074 204/424 |
| 6,019,881 A | * | 2/2000 | Kurosawa | G01N 27/4075 204/424 |
| 6,849,239 B2 | * | 2/2005 | Morris | G01N 33/0031 422/50 |
| 7,964,072 B2 | | 6/2011 | Wang et al. | |
| 2003/0205078 A1 | | 11/2003 | Hasei et al. | |

\* cited by examiner

*Primary Examiner* — Bach Dinh
(74) *Attorney, Agent, or Firm* — Joshua M. Haines (57) ABSTRACT

An $NO_2$ sensor comprises a sensing electrode material that includes a compound consisting essentially of one or more elements selected from the group consisting of Mn, Co, and Fe; an element selected from the group consisting of Si and Ti; and oxygen. In an alternate embodiment, the sensing electrode material includes a compound consisting essentially of one or more elements selected from the group consisting of Mn, Co, and Fe; an element selected from the group consisting of Si and Ti; an element selected from the group consisting of Mg, Al, Li, Na, and K; and oxygen. Sensors made with these sensing electrode materials demonstrate good $NO_2$ sensitivity and reduced sensitivity to cross-interference from NO and $NH_3$.

8 Claims, 4 Drawing Sheets

SENSOR MATERIAL AND GAS SENSOR ELEMENT AND GAS SENSOR DERIVED THEREFROM

BACKGROUND

Exhaust gas generated by combustion of fossil fuels in furnaces, ovens, and engines contain, for example, nitrogen oxides ($NO_X$, including mainly NO and $NO_2$), unburned hydrocarbons (HC), and carbon monoxide (CO), which are undesirable pollutants. Vehicles, e.g., diesel vehicles, utilize various pollution-control after treatment devices (such as a $NO_X$ absorber(s) and/or Selective Catalytic Reduction (SCR) catalyst(s)), to reduce $NO_X$. For diesel vehicles using SCR catalysts, $NO_X$ can be converted to $N_2$ and $H_2O$ by using ammonia ($NH_3$) gas. However, NO and $NO_2$ have very different reaction rates within an SCR converter. Additionally, the presence of $NH_3$ can also interfere with various types of $NO_X$ sensors, thereby reducing their accuracy. In order for SCR catalysts to work efficiently and to avoid pollution breakthroughs, more effective control systems are needed. The development of more effective control systems requires commercial $NO_X$ sensors with improved accuracy and sensitivity for a particular $NO_X$ constituent species and with reduced susceptibility to cross-interference from other $NO_X$ constituents and from $NH_3$.

For example, existing $NO_X$ sensing materials having the chemical composition of the general form $(AB)_2O_4$ or (AB)$O_3$, which include stoichiometric amounts of A, where A is metal elements capable of +3 valence state, and B, where B is Fe or Cr, are sensitive to $NO_X$. They are used as electrode materials in electrochemical devices for $NO_X$ sensing by virtue of the fact that they generate an electromotive force (emf) when exposed to $NO_X$, the magnitude and polarity of which may be characterized using the non-equilibrium Nernst Equation. However, generally, they show cross-sensitivity to $NH_3$ which tends to limit their usefulness to applications where $NH_3$ is not a concern. In addition, the individual contributions of NO and $NO_2$ to their $NO_X$ electromotive force (emf) outputs cannot readily be isolated. As such, while useful in some applications, these sensors are not generally suitable for applications that require $NO_2$ sensors having minimum cross-interference with NO and $NH_3$, or relatively larger $NO_2$ emf outputs (i.e., improved signal-to-noise performance) or both.

Thus, cost effective $NO_2$ sensors having reduced cross-sensitivity to NO and $NH_3$, or relatively high emf outputs or both, that can reliably sense $NO_2$ under exhaust gas conditions would be desirable for use in various $NO_2$ control systems.

SUMMARY OF THE INVENTION

An NO2 sensor material that may be used to make sensor elements having reduced cross-sensitivity to NO and $NH_3$, or relatively high emf outputs, or both, that can reliably sense $NO_2$ under exhaust gas conditions is described herein.

In one aspect, an $NO_2$ sensor material includes a compound selected from a first group consisting of oxides of Co, Fe, and Mn; and a compound selected from a second group consisting of $SiO_2$ and $TiO_2$. The $NO_2$ sensor material may be used in a sensor element of an $NO_2$ sensor.

In another aspect, an $NO_2$ sensor material includes a compound selected from a first group consisting of oxides of Co, Fe, and Mn; a compound selected from a second group consisting of $SiO_2$ and $TiO_2$; and a constituent selected from a third group consisting of AlO, MgO, and oxides of an alkali element such as K, Na, or Li.

BRIEF DESCRIPTION OF THE DRAWINGS

Referring now to the drawings wherein like elements are numbered alike in the several figures:

FIG. 1 is an exploded view of an exemplary embodiment of a gas sensor element as described herein;

DETAILED DESCRIPTION OF THE INVENTION

The $NO_2$ sensor materials and sensor elements and cells described herein may be employed in various forms of $NO_2$ sensors, or any type of gas sensor element where $NO_2$ sensing can be advantageous. Non-limiting examples of gas sensor elements where $NO_2$ sensing can be advantageous include $O_2$ sensors, $H_2$ sensors, CO sensors, HC sensors, and $NH_3$ sensor elements. A combination comprising at least one of the foregoing can also be used.

Referring now to FIG. 1, an exploded view of an exemplary gas sensor element 10 is shown. It is to be understood that although the invention is described in relation to a flat plate sensor, other two and three dimensional sensor designs can also be employed, such as conical, cylindrical, and the like, which also employ the arrangement of the elements described herein in a different physical configuration.

Referring to FIG. 1, an exemplary sensing element 10 includes an $NO_2$ sensing cell (12/16/14) including a first sensing electrode 12, a first reference electrode 14 and an electrolyte layer 16. The $NO_2$ sensing cell 12/16/14 is disposed at a sensing end 21 of the sensing element 10. The sensing element 10 includes insulating layers 22, 24, 28, 30, 32, 34, 36, 38, and active layers, which include the electrolyte layer 16 and layer 26. The active layers can conduct oxygen ions, where the insulating layers can insulate sensor components from electrical and ionic conduction. In an exemplary embodiment, the electrolyte layer 16 is disposed between insulating layers 22 and 24, and active layer 26 is disposed between insulating layers 24 and 28.

The sensing element 10 can further include a temperature sensor (not shown), an air-fuel sensing cell comprising the active layer 26 along with an electrode 80 and an electrode 82 (80/26/82), a heater 44 disposed between the insulating layers 36 and 38, and an electromagnetic shield 42 (also known as a ground plane layer) disposed between the insulating layers 34 and 36. A first inlet 94 is defined by a first surface of the insulating layer 24 and by a surface of the electrolyte 16, proximate the first reference electrode 14. A second inlet 96 is defined by a first surface of the active layer 26 and a second surface of the insulating layer 24, proximate the electrode 80. A third inlet 98 is defined by a second surface of the active layer 26 and a first surface of the insulating layer 28, proximate the electrode 82. In addition, the sensing element 10 includes electrical leads 58, contact pads 60, 62, 70, 76, 90, 92, and may include additional ground plane layer(s) (not shown), and the like.

The first sensing electrode 12 is disposed in physical and ionic communication with electrolyte 16 and can be disposed in fluid communication with a sample gas (e.g., a gas being monitored or tested for its $NO_2$ concentration). Referring to FIG. 1, this physical and ionic communication between electrolyte 16 and first sensing electrode 12 may be effected by forming insulating layer 22 with openings corresponding to and located under first electrode 12, which extend through insulating layer 22, thereby allowing the sensing electrode material disposed on the top surface of insulating layer 22 to extend through the opening and provide physical and ionic communication with an upper surface of electrolyte 16. In one embodiment, the sensing electrode material may be screen printed onto an assembly of the insulating layer 22 and electrolyte 16 and fired such that it extends through the opening and makes the necessary physical and ionic communication with electrolyte 16. The electrode materials have $NO_2$ sensing capability (e.g., catalyzing $NO_2$ gas to produce an emf), electrical conducting capability (conducting electrical current produced by the emf), and gas diffusion capability (providing sufficient open porosity so that gas can diffuse throughout the electrode and to the interface region of the electrode 12 and electrolyte 16.

The first sensing electrode 12 is made from a material with the above properties at the selected operating temperatures. In an exemplary embodiment, the sensing electrode material includes a compound consisting essentially of one or more elements selected from the group consisting of Mn, Co, and Fe; an element selected from the group consisting of Si and Ti; and oxygen. In an alternate embodiment, the sensing electrode material includes a compound consisting essentially of one or more elements selected from the group consisting of Mn, Co, and Fe; an element selected from the group consisting of Si and Ti; an element selected from the group consisting of Mg, Al, Li, Na, and K; and oxygen.

The $NO_2$ sensing electrode materials may be made by any suitable method. In an exemplary embodiment, the sensing electrode material may be made by mixing powders of metal oxide precursors having the desired constituent elements in amounts sufficient to provide the desired stoichiometric composition. Metal oxide precursors can be metal oxides, or any material comprising the metal that can oxidize under during processing of the powders to form the sensing electrode, such as by sintering in air of the metal oxide precursor powder mixture to form the $NO_2$ sensing electrode material. By way of non-limiting example, the powders may include a compound selected from a first group consisting of CoO, FeO, and MnO; and a compound selected from a second group consisting of $SiO_2$ and $TiO_2$. The compound may also include an element selected from a third group consisting of Mg, Al, Li, Na, and K.

The metal oxide precursors are used in an amount depending on the desired final microstructure and composition of the $NO_2$ sensing electrode material, and can be easily determined by a person of ordinary skill in the art. The metal oxide precursors are mixed using any suitable method to produce an intimate homogeneous mixture, such as by milling, by using a mortar and pestle, or the like. After mixing, the metal oxide precursor powders are heated to a temperature and for a time sufficient to form the desired $NO_2$ sensing electrode material composition. The heating may be done in air, but it is believed that for some combinations, heating other atmospheres or in vacuum may be desirable.

After the formation of the desired $NO_2$ sensing electrode material, it is disposed on the solid electrolyte 16 to form first $NO_2$ sensor cell 12/16/14, comprising sensing electrode 12. This can be effected using any suitable deposition application or other technique available to one with ordinary skill in the art including, but not limited to, spray coating, painting, dip coating, screen printing, laminating, and the like.

In one advantageous embodiment, disposing is effected by screen printing. In this embodiment, the $NO_2$ sensing electrode material can be made into an ink, which also refers to a paste or other fluid form suitable for screen printing, and disposed onto the insulating layer 22 in contact solid electrolyte 16.

The ink can further comprise a binder, a carrier, a wetting agent, and the like, and combinations comprising at least one of the foregoing. The binder can be any material capable of providing adhesion between the ink and the substrate. Non-limiting examples of binders include acrylic resin, acrylonitrile, styrene, poly(acrylic acid), poly(methacrylic acid), poly(methyl acrylate), poly(methyl methacrylate), and the like, as well as combinations comprising at least one of the foregoing binders. Carriers include any material suitable for imparting desired printing, drying, and rheological characteristics of the ink. Non-limiting examples of carriers include volatile solvents which can dissolve polymer resins such as butyl acetate. Non-limiting examples of wetting agents include ethanol, isopropyl alcohol, methanol, cetyl alcohol, calcium octoate, zinc octoate and the like, as well as combinations comprising at least one of the foregoing.

The different constituents of the ink can be present in different amounts depending on the nature of the materials, and the product, and can be readily determined by a person with ordinary skill in the art. In general, the binder can be present in about 1 to about 40 wt %, the carrier can be present in about 1 to about 40 wt %, the wetting agent can be present in about 1 to about 20 wt %, and the $NO_2$ sensing electrode material can be present in about 15 to about 98 wt %, based on the total weight of the ink.

Fugitive materials can also be used in the ink formulations to produce a desired porosity in the final $NO_2$ sensing electrode, that is, a sufficient porosity to enable the $NO_2$ to enter the $NO_2$ sensing electrode and reach triple points (points where the electrode, electrolyte, and $NO_2$ meet to enable the desired electrochemical reactions). Fugitive materials are materials that degrade leaving voids upon firing. Some non-limiting examples of fugitive materials include graphite, carbon black, starch, nylon, polystyrene, latex, other soluble organics (e.g., sugars and the like), and the like, as well as combinations comprising one or more of the foregoing fugitive materials. The fugitive material can be present in an amount of about 0.1 to about 20 wt %, based on the total weight of the ink.

The reference electrode 14 is disposed in physical contact and in ionic communication with the electrolyte 16, and can be disposed in fluid communication with the sample gas or reference gas; preferably with the sample gas. The reference electrode materials have oxygen catalyzing capability (e.g., catalyzing equilibrium $O_2$ gas to produce an emf), electrical conducting capability (conducting electrical current produced by the emf), and/or gas diffusion capability (providing sufficient open porosity so that gas can diffuse throughout the electrode and to the interface region of the reference electrode 14 and electrolyte 16). Possible reference electrode materials include platinum (Pt), palladium (Pd), osmium (Os), rhodium (Rh), iridium (Ir), gold (Au), ruthenium (Ru), and the like, as well as mixtures or alloys comprising at least one of the foregoing materials. The electrode can include metal oxides such as zirconia and alumina that can increase the electrode porosity and increase the contact area between the electrode and the electrolyte. With respect to the size and geometry of the reference electrode 14, it is generally adequate to provide current output sufficient to effect a reasonable signal resolution over a wide range of $NO_2$ concentrations. Generally, a thickness of about 1 to about 25 μm can be employed, more specifically a thickness of about 5 to about 20 μm, and even more specifically a thickness of about 10 to about 18 μm. The reference electrode 14 can be formed using any suitable technique such as chemical vapor deposition, screen printing, sputtering, and stenciling, among others, in any combination, with screen printing of inks or pastes that include the electrode material onto appropriate tapes being advantageous due to simplicity, economy, and compatibility with the subsequent firing process. For example, reference electrode 14 can be screen printed onto an abutting layer 24 or the underside of the solid electrolyte. Further, the reference electrode 14 can be embedded within either of the above layers.

The electrolyte layer 16 has oxygen ion conducting and fluid separation (limiting fluid communication of the sample gases on each side of the electrolyte layer 16) capabilities. The electrolyte layer 16 can be any size capable of providing sufficient ionic communication for the $NO_2$ sensing cell (12/16/14). The electrolyte layer 16 can be the entire length and width of the sensing element 10 or portions thereof. Any suitable electrolyte layer material having these characteristics may be used. Possible electrolyte layer materials include zirconium oxide (zirconia), cerium oxide (ceria), calcium oxide, yttrium oxide (yttria), lanthanum oxide, magnesium oxide, alumina oxide (alumina), indium oxide and the like, as well as combinations comprising at least one of the foregoing electrolyte materials, such as yttria doped zirconia, $LaGaO_3$, $SrCeO_3$, $BaCeO_3$, and $CaZrO_3$. These electrolyte materials may also include various dopants, alloying additions or other modifiers used to promote, prevent, stabilize or otherwise produce a desired microstructural affect, such as, for example, zirconia which is stabilized with respect to, among others, polymorphism, high temperature phase transformation, and the like, by the addition of calcium, barium, yttrium, magnesium, aluminum, lanthanum, cesium, gadolinium, ytterbium, scandium, or the like, or oxides thereof. The solid electrolyte layer 16 can be formed using any method available to one with ordinary skill in the art including, but not limited to, doctor blade slurry casting, tape casting, die pressing, roll compaction, stenciling, screen printing, and the like.

The air-fuel sensing cell (80/26/82) can detect the air to fuel ratio of the sample gas. When a constant potential is applied to electrodes 80 and 82, the current through the air-fuel sensing cell 80/26/82 is limited by the oxygen available in the inlets 96, or 98 and at the electrodes 80, 82. Therefore, by measuring the limiting current at the air-fuel sensing cell 80/26/82, the processor can determine the air-to-fuel ratio of the gas. This same cell can also be used for sensing the temperature of the gas. In this mode an AC signal will be applied to the electrode 80 and 82, and the impedance of the electrolyte 26 between the two electrodes 80 and 82 is used for temperature determination.

The heater 44 can be employed to maintain the sensing element 10 at a selected operating temperature. The heater 44 can be positioned as part of the monolithic design of the sensing element 10, for example between insulating layer 36 and insulating layer 38, in thermal communication with the air-fuel sensing cell 80/26/82 and the sensing cell 12/16/14. In other embodiments, the heater could be in thermal communication with the cells without necessarily being part of a monolithic laminate structure with them, e.g., simply by being in close physical proximity to a cell. More specifically, the heater can be capable of maintaining the sensing end 21 of the sensing element 10 at a sufficient temperature to facilitate the various electrochemical reactions therein. The heater can be a resistance heater and can comprise a line pattern (connected parallel lines, serpentine, and/or the like (not shown)). The heater can comprise, for example, platinum, aluminum, palladium, and the like, as well as combinations comprising at least one of the foregoing, oxides comprising at least one of the foregoing metals. Contact pads, for example, the fourth contact pad 90 and the fifth contact pad 92, can transfer current to the heater from an external power source.

The temperature sensor (not shown) comprises any temperature sensor capable of monitoring the temperature of the sensing end 21 of the sensing element 10 such as, for example, an impedance-measuring device or a metal-like resistance-measuring device. The metal-like resistance temperature sensor can comprise, for example, a line pattern (connected parallel lines, serpentine, and/or the like). Some possible materials include, but are not limited to, electrically conductive materials such as metals including platinum (Pt), copper (Cu), silver (Ag), palladium (Pd), gold (Au), tungsten (W), as well as combinations comprising at least one of the foregoing.

Disposed between the insulating layers 34 and 36 can be an electromagnetic shield 42. The electromagnetic shield 42 isolates electrical influences by dispersing electrical interferences and creating a barrier between a high power source (such as the heater) and a low power source (such as the air-fuel ratio sensor, the temperature sensor, and the gas sensing cell). The shield can comprise, for example, a line pattern (connected parallel lines, serpentine, cross hatch pattern, and/or the like). Any suitable electrically conductive material may be used. Some possible materials for the shield can include, without limitation, those materials discussed above for the heater or temperature sensor.

At the sensing end 21 of the sensing element 10, the electrical leads 58, are disposed in physical contact and in electrical communication with electrodes 12, 14, 80, 82. In an exemplary embodiment, electrodes 80 and 82 and their associated electrical leads are disposed on an upper and a lower surface of electrolyte 26. Further, electrical leads 58 are disposed in electrical communication with the heater 44 and the electromagnetic shield 42. Each electrical lead extends from a contact pad or via toward the sensing end 21. Electrical leads not disposed on a top surface or a bottom surface of the sensing element 10 are in electrical communication with the contact pads through vias formed in the layers. Two sets of three contact pads are disposed at the terminal end 81 of the sensing element 10: the first, second, and third contact pads 60, 70, 76, respectively, are disposed on the upper surface of the sensing element 10, and the fourth, fifth and sixth contact pads 62, 90, 92, respectively, are disposed on the lower surface of the sensing element 10. The first, second, third, and fourth contact pads 60, 62 70, 76 are in electrical communication with a controller (not shown), and the fifth and sixth contact pads 90, 92 are in electrical communication with an external power source (not shown) which may also be incorporated into or associated with a controller or controllers, including various microprocessor-based controllers.

The insulating layers 22, 24, 28, 30, 32, 34, 36, 38 can comprise a dielectric material such as alumina (i.e., aluminum oxide ($Al_2O_3$)), other insulating ceramics, and the like. Each of the insulating layers can comprise a sufficient thickness to attain the desired insulating and/or structural properties. For example, each insulating layer can have a thickness of about 1 up to about 200 micrometers or so, depending upon the number of layers employed, or, more specifically, a thickness of about 50 micrometers to about 200 micrometers. Further, the sensor element 10 can comprise additional insulating layers to isolate electrical devices, segregate gases, and/or to provide additional structural support.

The active layer 26 can include material that, while under the operating conditions of sensing element 10, is capable of permitting the electrochemical transfer of oxygen ions. These include the same or similar materials to those described as comprising electrolyte layer 16. Each of the active layers can comprise a thickness of up to about 200 micrometers or so, depending upon the number of layers employed, or, more specifically, a thickness of about 50 micrometers to about 200 micrometers.

Figure 2:
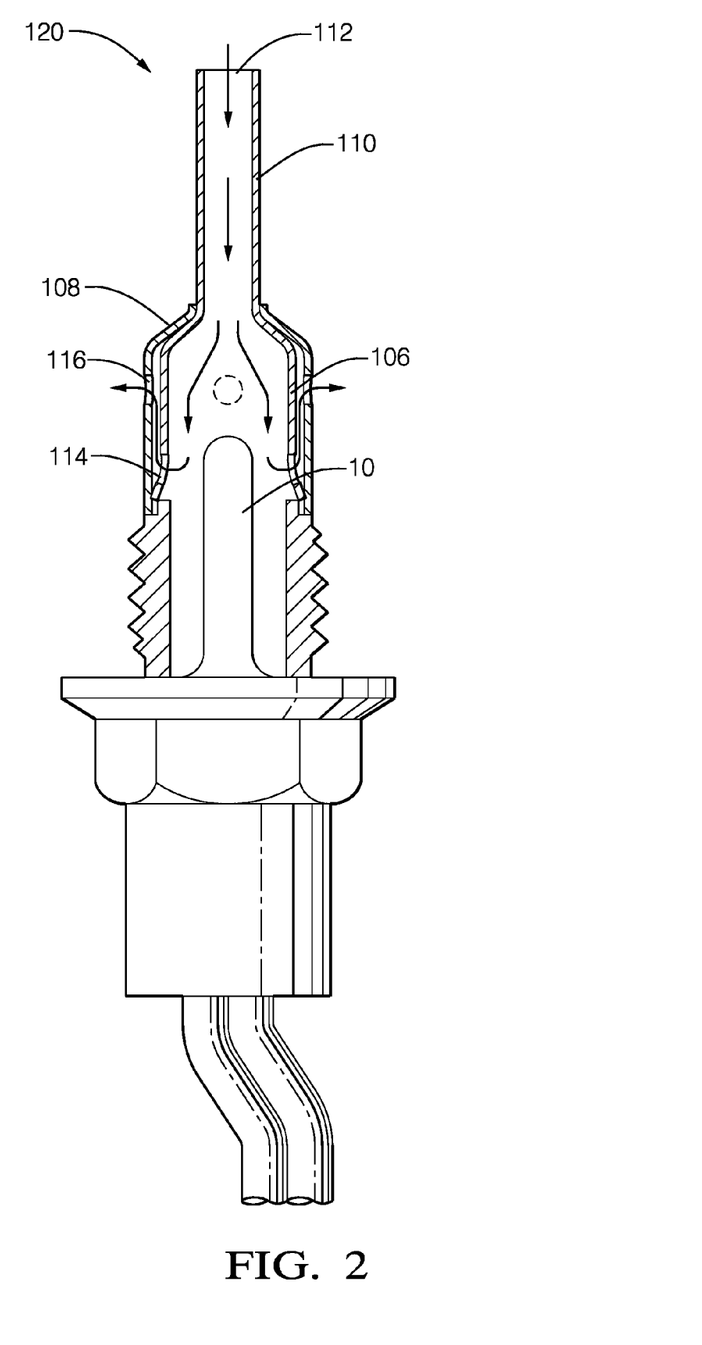
FIG. 2 is a cross-sectional view of an exemplary embodiment of a gas sensor that includes a sensor element, as described herein.

Referring to FIG. 2, for placement in a gas stream, gas sensor element 10 can be disposed within a protective casing 120. The protective casing 120 can comprise an outer shield 108 having a plurality of outer shield holes 116. An inner shield 106 has a plurality of passages 114, which allows fluid to enter a space between the inner shield 106 and the outer shield 108. Outer shield holes 116 allow fluid in the space between inner shield 106 and outer shield 108 to exit the casing 120. An optional sampling tube 110 having an inlet 112 extends from the outer shield 108. Arrows are shown to illustrate the general fluid flow direction within the protective casing.

The plurality of exhaust passages 114 may be disposed through inner shield 106 to allow the exhaust fluid a sufficient time to contact the sensing element 10 prior to exiting the protective casing 120. The plurality of exhaust passages 114 can be any size or shape sufficient to allow the passage of exhaust fluid.

Suitable materials for the protective casing 120 can include materials that are capable of resisting under-car salt and other contaminants, operating temperatures, and corrosion. For example, ferrous materials are employed including various stainless steels, such as terrific stainless steels. Ferritic stainless steels may include stainless steels such as, e.g., SS-409, SS-316, and the like.

The sensing element 10 can be formed using any suitable method, including various ceramic processing techniques. For example, milling processes (e.g., wet and dry milling processes including ball milling, attrition milling, vibration milling, jet milling, and the like) can be used to size ceramic powders into desired particle sizes and desired particle size distributions to obtain physical, chemical, and electrochemical properties. The ceramic powders can be mixed with plastic binders to form various shapes. For example, the structural components (e.g., insulating layers 22, 24, 28, 30, 32, 34, 36, and 38 and the active or electrolyte layers 16, 26) can be formed into "green" tapes by tape-casting, role-compacting, or similar processes. The non-structural components (e.g., the first electrode 12, the reference electrode 14, the electrical leads, and the contact pads) can be formed into a tape or can be deposited onto the structural components by any suitable method, including various ceramic processing techniques (e.g., sputtering, painting, chemical vapor deposition, screen-printing, stenciling, and the like).

The inlets 94, 96, 98, can be formed either by disposing fugitive material (material that will dissipate during the sintering process, e.g., graphite, carbon black, starch, nylon, polystyrene, latex, other insoluble organics, as well as compositions comprising one or more of the foregoing fugitive materials) or by disposing material that will leave sufficient open porosity in the fired ceramic body to allow gas diffusion therethrough. Once the "green" sensor is formed, the sensor can be sintered at a selected firing cycle to allow controlled burn-off of the binders and other organic materials and to form the ceramic material of the sensor with the desired physical, microstructural, compositional and other properties described herein.

The first $NO_2$ sensing cell 12/16/14 can generate an emf as described by the Nernst Equation, particularly as adapted for use under non-equilibrium conditions. In the exemplary embodiment, the sample gas is introduced to the sensing electrode and is diffused throughout the porous electrode materials. In the sensing electrode, the materials induce electrochemical reactions in the sample gas. These reactions include catalyzing $NO_2$ to $O^{-2}$ and NO. Similarly, in the reference electrode 14 catalytic material induces catalytic reactions in the reference gas, converting equilibrium oxygen gas ($O_2$) to oxide ions ($O^{-2}$) or vice versa, and thereby producing an emf. Therefore, the electrical potential difference between the sensing electrode 12 and the corresponding reference electrode 14 can be measured to determine an emf.

The reactants at electrodes of the first $NO_2$ sensing cell 12/16/14 may include $NH_3$, NO, $NO_2$, CO, HC, $H_2O$, and $O_2$. The partial pressure of reactive components at the electrodes of the $NO_2$ sensing cell(s) can be determined from the cell's electromotive force (emf) by using the non-equilibrium Nernst Equation (1):

$$EMF \approx a\frac{kT}{e}\text{Ln}(P_{NH_3}) - b\frac{kT}{e}\text{Ln}(P_{NO}) - c\frac{kT}{e}\text{Ln}(P_{NO_2}) - d\frac{kT}{e}\text{Ln}(P_{CO}) - g\frac{kT}{e}\text{Ln}(P_{HC}) - h\frac{kT}{e}\text{Ln}(P_{H_2O}) - i\frac{kT}{e}\text{Ln}(P_{O_2}) + \text{constant} \quad (1)$$

where: k=the Boltzmann constant
T=the absolute temperature of the gas
e=the electron charge unit
a, b, c, d, g, h, i are constants
Ln=natural log function
$P_{NH_3}$=the partial pressure of ammonia in the gas,
$P_{NO}$=the partial pressure of nitrogen monoxide in the gas
$P_{NO_2}$=the partial pressure of nitrogen dioxide in the gas
$P_{CO}$=the partial pressure of carbon monoxide in the gas
$P_{HC}$=the partial pressure of hydrocarbon in the gas
$P_{H_2O}$=the partial pressure of water vapor in the gas
$P_{O_2}$=the partial pressure of oxygen in the gas The temperature sensor can measure a temperature indicative of the absolute gas temperature (T). The oxygen and water vapor content, e.g., partial pressures, in the unknown gas can be determined from the air-fuel ratio as measured by the air-fuel sensing cell 80/26/82.

The air to fuel ratio can be obtained by a controller, such as an engine control module (ECM) as described, for example in GB2347219A, or by having an air to fuel ratio sensor integrated into the sensor 10. Alternatively, a complete mapping of $H_2O$ and $O_2$ concentrations under all engine running conditions (measured by instruments such as mass spectrometer) can be obtained empirically and stored in ECM in a look-up table with which the sensor is in signal communication. Once the oxygen and water vapor content information is known, the controller can use the information to more accurately determine the partial pressures of the sample gas components. Typically, the water and oxygen correction according to Equation (1) is a small number within the water and oxygen ranges of diesel engine exhaust.

The advantageous performance of the $NO_2$ sensing electrode materials described herein and their applicability to gas sensor elements and gas sensors which include $NO_2$ sensing capability is illustrated by the examples provided below.

EXAMPLE 1

The composition of the sensor material in this example was $MnSiO_3$. It is made of MnO and $SiO_2$ powders, mechanically mixed and fired at 1150° C. for ten hours to produce a powder of an oxide having the chemical composition indicated above. The oxide was formulated into a thick film ink as described herein, printed onto the surface of an electrolyte layer as described herein, fired at 1000° C. for one hour, and assembled into a sensor element as described herein. The sensor element was fabricated into an $NO_2$ sensor as described herein. The $NO_2$ sensor was used to make emf measurements at several concentrations of $NH_3$, NO, $NO_2$, CO, HC, in order to evaluate the performance of the sensor elements and, more particularly, the performance of the oxide material described above as an $NO_2$ sensor material and its sensitivity to other gases.

Figure 3:
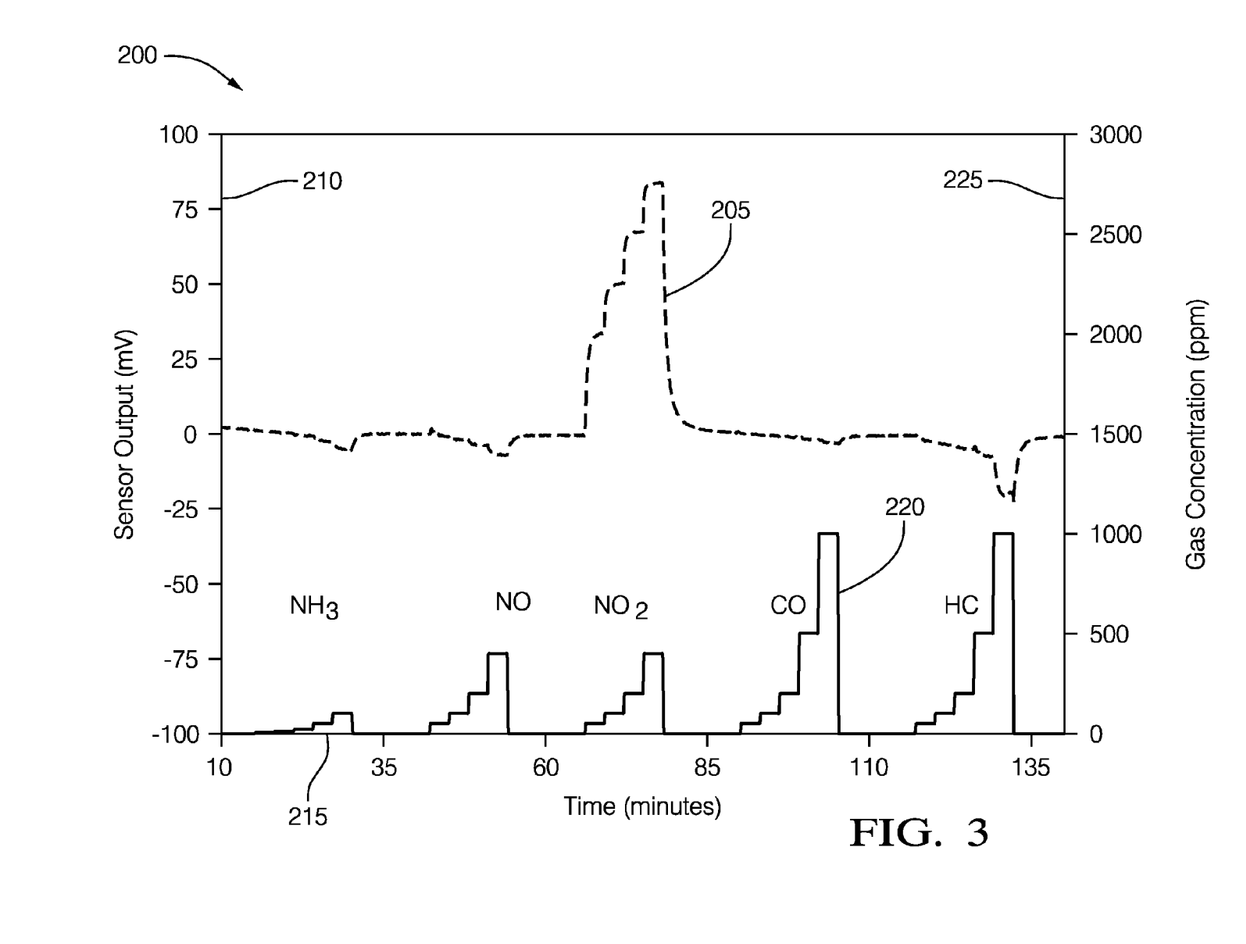
FIG. 3 is a graphical representation of emf output vs. time for a gas sensor including aspects of the present invention in response to varying concentrations of various exhaust gas constituents.

The results for Example 1 are illustrated in FIG. 3. FIG. 3 includes a plot 200 which includes a trace 205 that represents the output voltage of the sensor, plotted against the y-axis 210 on the left side of the plot 200, as a function of time represented on the x-axis 215. The sensor was exposed to several levels of several gases of interest in a carrier gas, where the carrier gas was 7.4% volume percent $H_2O$ balanced with 1.0% volume percent $O_2$, with the remainder of the gas $N_2$. Trace 205 represents the emf output of the sensor for various concentrations of each of the several gas compositions with respect to time. Plot 200 in FIG. 3 also includes a trace 220, which represents the concentration in ppm of each of the gases of interest, plotted against the second y-axis 225 on the right side of the chart. There are five different zones on the chart 200, with each zone corresponding to one of the gases of interest. The first zone, corresponding to a time range from about 10 minutes to about 35 minutes, corresponds to exposure of the sensor to $NH_3$ gas at concentrations of 0, 5, 10, 20, 50, 100 and 0 PPM in the carrier gas. The second zone, corresponding to a time range from about 35 minutes to about 60 minutes, corresponds to exposure of the sensor to NO gas at concentrations of 0, 50, 100, 200, 400 and 0 PPM in a carrier gas. The third zone, corresponding to a time range from about 60 minutes to about 85 minutes, corresponds to exposure of the sensor to $NO_2$ gas at concentrations of 0, 50, 100, 200, 400 and 0 PPM in the carrier gas. The fourth zone, corresponding to a time range from about 85 minutes to about 110 minutes, corresponds to exposure of the sensor to CO gas at concentrations of 0, 50, 100, 200, 500, 1000, and 0 PPM in the carrier gas. The fifth zone, corresponding to a time range from about 110 minutes to about 135 minutes, corresponds to exposure of the sensor to $C_3H_6$ gas at concentrations of 0, 50, 100, 200, 500, 1000, and 0 PPM in the carrier gas. As may be seen, the exemplary composition of the sensor material in this example, $MnSiO_3$, showed good sensitivity to $NO_2$ and very little susceptibility to cross-interference from $NH_3$ NO, CO, and HC.

Figure 4:
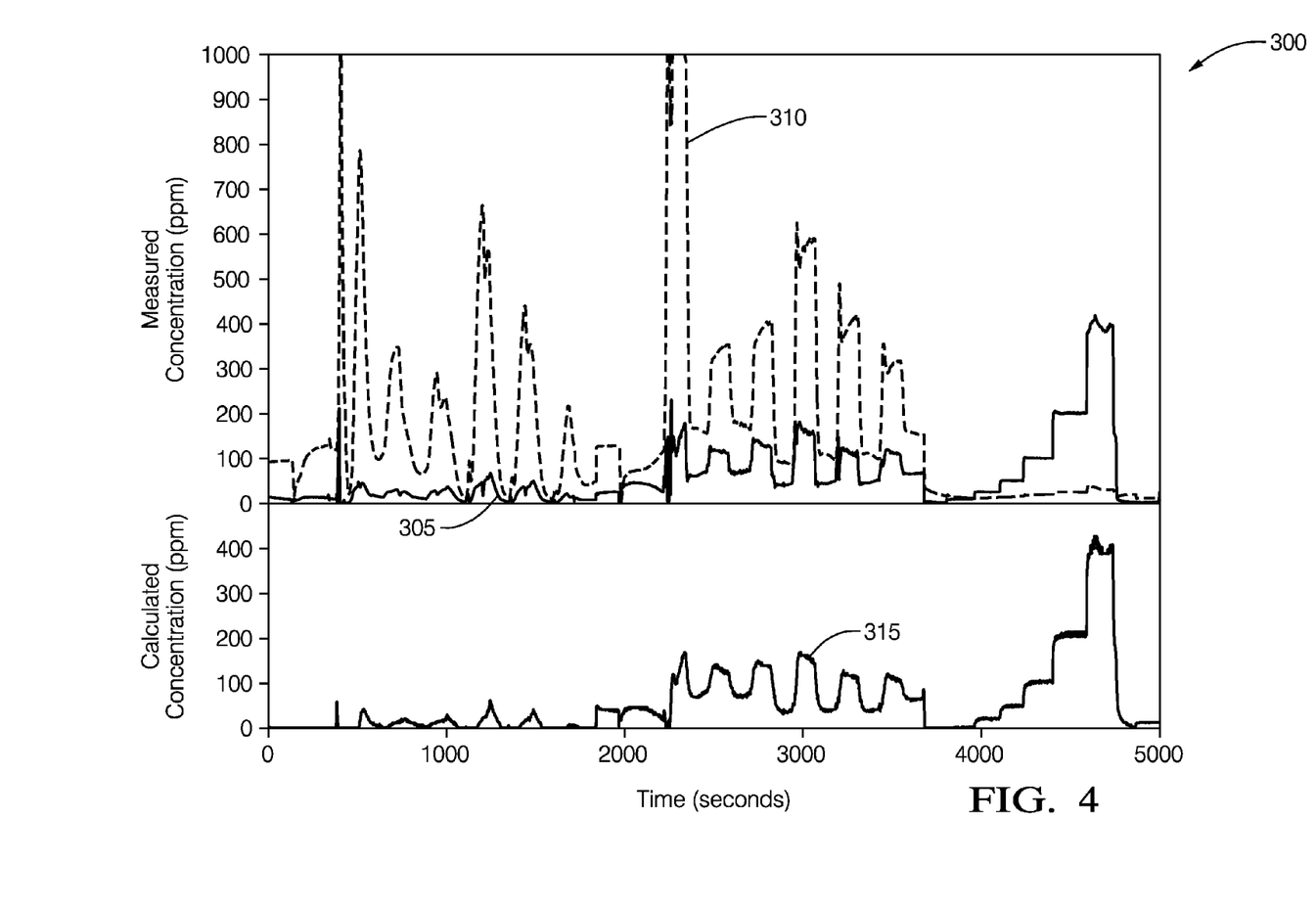
FIG. 4 is a graphical representation of measured $NO_2$ concentration and measured NO concentration according to laboratory instrumentation, and $NO_2$ concentration as indicated by a sensor incorporating aspects of the present invention, during an engine test cycle.

FIG. 4 is a plot 300 that includes results obtained during engine testing on a transient ESC (European Stationary Cycle) emissions test. In FIG. 4, the top solid trace 305 represents measured $NO_2$ in the engine exhaust, and the top dashed trace 310 represents measured NO in the engine exhaust, where the measurements for both were made using a gas bench as the exhaust gas composition analyzer. During the test the emf of a sensor exposed to the engine exhaust was recorded, the sensor having a sensing electrode 12 comprising $MnSiO_3$ as described by Example 1. The emf readings from the sensor were converted to ppm using the inverse of Equation 1 above. With continued reference to FIG. 4, the calculated ppm concentration of $NO_2$ as indicated by the sensor is presented as the solid trace 315 at the bottom of plot 300. As demonstrated in FIG. 4, there is good correlation between the $NO_2$ concentration measured by a laboratory gas analyzer (trace 305) and the $NO_2$ concentration measured by a sensor having a sensing electrode comprising $MnSiO_3$ (trace 315). Even in the presence of high concentrations of NO in the measured gas (as evidenced by trace 310 in FIG. 4), the sensing electrode 12 comprising $MnSiO_3$ is shown to be a good electrode material for $NO_2$ sensing.

EXAMPLE 2

The composition of the sensor material in this example was $Mn_2SiO_4$. It is made of MnO and $SiO_2$ powders, mechanically mixed and fired at 1150° C. for ten hours to produce a powder of an oxide having the chemical composition indicated above. The oxide was formulated into a thick film ink as described herein, printed onto the surface of an electrolyte layer as described herein, fired at 1000° C. for one hour, and assembled into a sensor element as described herein. The sensor element was fabricated into an $NO_2$ sensor as described herein. The $NO_2$ sensor was used to make emf measurements at known concentrations of $NH_3$, NO, and $NO_2$, in order to evaluate the performance of the sensor elements and, more particularly, the performance of the oxide material described above as an $NO_2$ sensor material and its sensitivity to other gases.

EXAMPLE 3

The composition of the sensor material in this example was $Mn_{1.7}SiO_{3.7}$. It is made of MnO and $SiO_2$ powders, mechanically mixed and fired at 1150° C. for ten hours to produce a powder of an oxide having the chemical composition indicated above. The oxide was formulated into a thick film ink as described herein, printed onto the surface of an electrolyte layer as described herein, fired at 1050° C. for one hour, and assembled into a sensor element as described herein. The sensor element was fabricated into an $NO_2$ sensor as described herein. The $NO_2$ sensor was used to make emf measurements at known concentrations of $NH_3$, NO, and $NO_2$, in order to evaluate the performance of the sensor elements and, more particularly, the performance of the oxide material described above as an $NO_2$ sensor material and its sensitivity to other gases.

EXAMPLE 4

The composition of the sensor material in this example was $Co_2SiO_4$. It is made of CoO and $SiO_2$ powders, mechanically mixed and fired at 1250° C. for thirty hours to produce a powder of an oxide having the chemical composition indicated above. The oxide was formulated into a thick film ink as described herein, printed onto the surface of an electrolyte layer as described herein, fired at 1125° C. for one hour, and assembled into a sensor element as described herein. The sensor element was fabricated into an $NO_2$ sensor as described herein. The $NO_2$ sensor was used to make emf measurements at known concentrations of $NH_3$, NO, and $NO_2$, in order to evaluate the performance of the sensor elements and, more particularly, the performance of the oxide material described above as an $NO_2$ sensor material and its sensitivity to other gases.

EXAMPLE 5

The composition of the sensor material in this example was $CoTi_2O_5$. It is made of CoO and $TiO_2$ powders, mechanically mixed and fired at 1350° C. for ten hours to produce a powder of an oxide having the chemical composition indicated above. The oxide was formulated into a thick film ink as described herein, printed onto the surface of an electrolyte layer as described herein, fired at 1150° C. for one hour, and assembled into a sensor element as described herein. The sensor element was fabricated into an $NO_2$ sensor as described herein. The $NO_2$ sensor was used to make emf measurements at known concentrations of $NH_3$, NO, and $NO_2$, in order to evaluate the performance of the sensor elements and, more particularly, the performance of the oxide material described above as an $NO_2$ sensor material and its sensitivity to other gases.

EXAMPLE 6

The composition of the sensor material in this example was $CoMnSiO_4$. It is made of CoO, MnO and $SiO_2$ powders, mechanically mixed and fired at 1250° C. for twenty hours to produce a powder of an oxide having the chemical composition indicated above. The oxide was formulated into a thick film ink as described herein, printed onto the surface of an electrolyte layer as described herein, fired at 1150° C. for one hour, and assembled into a sensor element as described herein. The sensor element was fabricated into an $NO_2$ sensor as described herein. The $NO_2$ sensor was used to make emf measurements at known concentrations of $NH_3$, NO, and $NO_2$, in order to evaluate the performance of the sensor elements and, more particularly, the performance of the oxide material described above as an $NO_2$ sensor material and its sensitivity to other gases.

EXAMPLE 7

The composition of the sensor material in this example was $Fe_2SiO_4$. It is made of FeO and $SiO_2$ powders, mechanically mixed and fired at 1050° C. for ten hours to produce a powder of an oxide having the chemical composition indicated above. The oxide was formulated into a thick film ink as described herein, printed onto the surface of an electrolyte layer as described herein, fired at 1050° C. for one hour, and assembled into a sensor element as described herein. The sensor element was fabricated into an $NO_2$ sensor as described herein. The $NO_2$ sensor was used to make emf measurements at known concentrations of $NH_3$, NO, and $NO_2$, in order to evaluate the performance of the sensor elements and, more particularly, the performance of the oxide material described above as an $NO_2$ sensor material and its sensitivity to other gases.

EXAMPLE 8

The composition of the sensor material in this example was $MnTiO_3$. It is made of MnO and $TiO_2$ powders, mechanically mixed and fired at 1150° C. for ten hours to produce a powder of an oxide having the chemical composition indicated above. The oxide was formulated into a thick film ink as described herein, printed onto the surface of an electrolyte layer as described herein, fired at 1000° C. for one hour, and assembled into a sensor element as described herein. The sensor element was fabricated into an $NO_2$ sensor as described herein. The $NO_2$ sensor was used to make emf measurements at several concentrations of $NH_3$, NO, $NO_2$, CO, HC, in order to evaluate the performance of the sensor elements and, more particularly, the performance of the oxide material described above as an $NO_2$ sensor material and its sensitivity to other gases.

EXAMPLE 9

The composition of the sensor material in this example was $Fe_2TiO_4$. Powder of an oxide having the chemical composition indicated above was purchased from a commercial source. The oxide was formulated into a thick film ink as described herein, printed onto the surface of an electrolyte layer as described herein, fired at 1000° C. for one hour, and assembled into a sensor element as described herein. The sensor element was fabricated into an $NO_2$ sensor as described herein. The $NO_2$ sensor was used to make emf measurements at several concentrations of $NH_3$, NO, $NO_2$, CO, HC, in order to evaluate the performance of the sensor elements and, more particularly, the performance of the oxide material described above as an $NO_2$ sensor material and its sensitivity to other gases.

The $NO_2$ sensing electrode component based on silicate compounds may also include an alkali element (e.g. Li, Na, or K) and/or an alkaline earth element (e.g. Mg) and/or alumina ($Al_2O_3$) in its structure, as illustrated by Examples 10-12 that follow.

EXAMPLE 10

The composition of the sensor material in this example was $MnMgSiO_4$. It is made of MnO, MgO, and $SiO_2$ powders, mechanically mixed and fired at 1250° C. for ten hours to produce a powder of an oxide having the chemical composition indicated above. The oxide was formulated into a thick film ink as described herein, printed onto the surface of an electrolyte layer as described herein, fired at 1050° C. for one hour, and assembled into a sensor element as described herein. The sensor element was fabricated into an $NO_2$ sensor as described herein. The $NO_2$ sensor was used to make emf measurements at several concentrations of $NH_3$, NO, $NO_2$, CO, HC, in order to evaluate the performance of the sensor elements and, more particularly, the performance of the oxide material described above as an $NO_2$ sensor material and its sensitivity to other gases.

EXAMPLE 11

The composition of the sensor material in this example was $Mn_{1.88}K_{0.07}Fe_{0.06}SiO_4$. It is made of MnO, $K_2CO_3$, $Fe_2O_3$, and $SiO_2$ powders, mechanically mixed and fired at 1150° C. for ten hours to produce a powder of an oxide having the chemical composition indicated above. The oxide was formulated into a thick film ink as described herein, printed onto the surface of an electrolyte layer as described herein, fired at 1050° C. for one hour, and assembled into a sensor element as described herein. The sensor element was fabricated into an $NO_2$ sensor as described herein. The $NO_2$ sensor was used to make emf measurements at several concentrations of $NH_3$, NO, $NO_2$, CO, HC, in order to evaluate the performance of the sensor elements and, more particularly, the performance of the oxide material described above as an $NO_2$ sensor material and its sensitivity to other gases.

EXAMPLE 12

The composition of the sensor material in this example was $Mn_{1.8}Al_{0.19}SiO_4$. It is made of MnO, $Al_2O_3$, and $SiO_2$ powders, mechanically mixed and fired at 1150° C. for fifteen hours to produce a powder of an oxide having the chemical composition indicated above. The oxide was formulated into a thick film ink as described herein, printed onto the surface of an electrolyte layer as described herein, fired at 1150° C. for fifteen hours, and assembled into a sensor element as described herein. The sensor element was fabricated into an $NO_2$ sensor as described herein. The $NO_2$ sensor was used to make emf measurements at several concentrations of $NH_3$, NO, $NO_2$, CO, HC, in order to evaluate the performance of the sensor elements and, more particularly, the performance of the oxide material described above as an $NO_2$ sensor material and its sensitivity to other gases.

Sensors having sensing electrode compositions as described by each of the foregoing Examples 1 through 12 were constructed. Each of these sensors can produce an emf output as a function of gas composition similar to the results presented for Example 1 in FIGS. 3 and 4. The emf output of each sensor was measured under individual gas dosing conditions of 100 ppm $NH_3$, 400 ppm NO, and 400 ppm $NO_2$ in a carrier gas, as well as baseline conditions of the carrier gas alone. These emf results, measured in mV, are summarized in Table 1 below. It will be noted that there are slight differences in the emf output of the sensor of Example 1 listed in Table 1 compared to the emf levels of the sensor of Example 1 presented in FIG. 3. These differences are due to the carrier gas used to produce FIG. 3 having levels of 1.0% $O_2$ and 7.4% $H_2O$ with the remainder $N_2$, while the carrier gas used to produce the measurements in Table 1 having levels of 10.5% $O_2$ and 7.4% $H_2O$ with the remainder $N_2$. While the sensor of Example 1 was found to be relatively insensitive to humidity, a sensitivity to oxygen concentration was observed that accounts for the differences in emf values between Table 1 and FIG. 3.

TABLE 1

| Sensor | Electrode Material | Base emf | 100 ppm $NH_3$ emf | 400 ppm NO emf | 400 ppm $NO_2$ emf |
|---|---|---|---|---|---|
| Example 1 | $MnSiO_3$ | −3 | −12 | −7 | 44 |
| Example 2 | $Mn_2SiO_4$ | −1 | −20 | −4 | 37 |
| Example 3 | $Mn_{1.7}SiO_{3.7}$ | 0 | −4 | −4 | 39 |
| Example 4 | $Co_2SiO_4$ | 0 | −11 | −2 | 46 |
| Example 5 | $CoTi_2O_5$ | 7 | −14 | −7 | 88 |
| Example 6 | $CoMnSiO_4$ | 7 | 1 | −2 | 58 |
| Example 7 | $Fe_2SiO_4$ | 7 | 0 | 1 | 60 |
| Example 8 | $MnTiO_3$ | 0 | −5 | −1 | 35 |
| Example 9 | $Fe_2TiO_4$ | 0 | −21 | −15 | 85 |
| Example 10 | $MnMgSiO_4$ | 0 | −7 | −8 | 46 |
| Example 11 | $Mn_{1.88}K_{0.07}Fe_{0.06}SiO_4$ | 0 | −4 | −4 | 46 |
| Example 12 | $Mn_{1.8}Al_{0.19}SiO_4$ | 0 | −7 | −7 | 46 |

All emf values in millivolts

The sensing electrode materials described herein enable the determination of $NO_2$ concentration in the presence of other gases that may be found in an engine exhaust gas mixture. The sensor and methods can be used for on board diagnostics (OBD) or other control applications for vehicle exhaust treatment systems, such as diesel exhaust treatment systems, and including various systems designed to control or otherwise reduce the $NO_2$ components of vehicle emissions.

It should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. As used herein, "combination" is inclusive of blends, mixtures, alloys, reaction products, and the like, as appropriate. The modifier "about" used in connection with a quantity is inclusive of the stated value and has the meaning dictated by the context (e.g., includes the degree of error associated with measurement of the particular quantity). Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.). Finally, unless defined otherwise, technical and scientific terms used herein have the same meaning as is commonly understood by one of skill in the art to which this invention belongs. The suffix "(s)" as used herein is intended to include both the singular and the plural of the term that it modifies, thereby including one or more of that term (e.g., the metal(s) includes one or more metals). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., it includes the degree of error associated with measurement of the particular quantity).

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An $NO_2$ sensor comprising a sensing electrode comprising a sensor material; said sensor material comprising a compound consisting essentially of Si and oxygen and expressed by ABD wherein oxygen is element D and wherein Si is element B and wherein element A includes one or more elements selected from the group consisting of Mn, Co, and Fe, wherein the sensor material comprises $Mn_2SiO_4$.

2. An $NO_2$ sensor comprising a sensing electrode comprising a sensor material; said sensor material comprising a compound consisting essentially of Si and oxygen and expressed by ABD wherein oxygen is element D and wherein Si is element B and wherein element A includes one or more elements selected from the group consisting of Mn, Co, and Fe, wherein the sensor material comprises $Mn_{1.7}SiO_{3.7}$.

3. An $NO_2$ sensor comprising a sensing electrode comprising a sensor material; said sensor material comprising a compound consisting essentially of Si and oxygen and expressed by ABD wherein oxygen is element D and wherein Si is element B and wherein element A includes one or more elements selected from the group consisting of Mn, Co, and Fe, wherein the sensor material comprises $Co_2SiO_4$.

4. An $NO_2$ sensor comprising a sensing electrode comprising a sensor material; said sensor material comprising a compound consisting essentially of Ti and oxygen and expressed by ABD wherein oxygen is element D and wherein Ti is element B and wherein element A includes one or more elements selected from the group consisting of Mn, Co and Fe, wherein the sensor material comprises $CoTi_2O_5$.

5. An $NO_2$ sensor comprising a sensing electrode comprising a sensor material; said sensor material comprising a compound consisting essentially of Si and oxygen and expressed by ABD wherein oxygen is element D and wherein Si is element B and wherein element A includes one or more elements selected from the group consisting of Mn, Co, and Fe, wherein the sensor material comprises $Fe_2SiO_4$.

6. An $NO_2$ sensor comprising a sensing electrode comprising a sensor material; said sensor material comprising a compound consisting essentially of Ti and oxygen and expressed by ABD wherein oxygen is element D and wherein Ti is element B and wherein element A includes one or more elements selected from the group consisting of Mn, Co and Fe, wherein the sensor material comprises $Fe_2TiO_4$.

7. An $NO_2$ sensor comprising a sensing electrode comprising a sensor material; said the sensor material is $Mn_{1.88}K_{0.07}Fe_{0.06}SiO_4$.

8. An $NO_2$ sensor comprising a sensing electrode comprising a sensor material; said sensor material comprising a compound consisting essentially of Si and oxygen and expressed by ACBD wherein oxygen is element D and wherein Si is element B and wherein element A includes one or more elements selected from the group consisting of Mn, Co, and Fe; and wherein element C includes an element selected from the group consisting of Mg, Al, Li, Na, and K, wherein the sensor material comprises $Mn_{1.8}Al_{0.19}SiO_4$.

* * * * *